United States Patent [19]

Moore

[11] Plant 4,026

[45] Mar. 29, 1977

[54] MINIATURE ROSE PLANT

[76] Inventor: Ralph S. Moore, 2519 E. Noble Ave., Visalia, Calif. 93277

[21] Appl. No.: 651,700

[22] Filed: Jan. 23, 1976

[51] Int. Cl.[2] ..... A01H 5/00

[52] U.S. Cl. ..... Plt./9

[58] Field of Search ..... Plt./9

*Primary Examiner*—Robert E. Bagwill

EXEMPLARY CLAIM

1. A new and distinct variety of miniature moss rose plant of hardy dwarf, rounded, much branched, bush type, as illustrated and described, characterized (1) by buds which are heavily covered with soft moss-like appendages — said "moss" covering the sepals and extending downward onto the peduncle, and (2) by buds and flowers resembling the Baby Pinocchio (U.S. Plant Pat. No. 2,967) miniature rose in general form and size, but less double, the color being a light shade of pink; the general color effect being light pink — of a shade resembling Fairy Moss (miniature — U.S. Plant Pat. No. 3,083); and further characterized by a plant which is of moderate vigor, compact growth habit with short internodes, easy to propagate by budding as well as by cuttings; with small semi-glossy to mat foliage; and flowers, produced recurrently throughout the growing season, borne singly or several to the stem in loose clusters.

1 Drawing Figure

The present invention relates to a new and distinct variety of hardy, dwarf, bush type rose plant of the miniature class; the variety being primarily characterized — as to novelty (A) by soft to medium pink buds and flowers which in general color effect are a light to medium pink similar in color to June Time (Miniature — U.S. Plant Pat. No. 2,563), and (B) by the well mossed buds.

The variety is further characterized by:

An abundance of bloom, with flowers borne singly or several to the stem in clusters.
Some fragrance.

A plant which is vigorous, of rounded spreading shape with mat to semi-glossy, moderately small foliage with pointed leaflets; the buds and flowers being similar in form and size to the variety Baby Pinocchio (Miniature — U.S. Plant Pat. No. 2,967), but less double. The plant, which has a normal height of 12 to 16 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between Fairy Moss (Miniature—U.S. Plant Pat. No. 3,083) as the seed parent and a very mossed unnamed seedling miniature rose as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers.

Referring now specifically to the new and distinct variety of miniature rose plant, the following is a detailed description thereof in outline; all major color plate identifications being by reference to the British Colour Council Horticulture Colour Chart, except where common terms of color definition are employed.

Type: Hardy; dwarf; bush; seedling; greenhouse; outdoors; cut flowers; garden decoration; potted plant.

Class: Miniature-Moss

Flowers:

*Continuity.*—Continuous — repeat bloom all season.

*Fragrance.*—Some.

Flowers borne: Singly and several together (3 to 5) on strong, short stems.

Quantity of bloom: Abundant both outside and in greenhouse.

Bud:

*Penduncle.*—Medium length; slender but sturdy; erect; medium green; covered with an abundance of soft thorns with moss-like modifications. Before calyx breaks; size — small. Form medium long; pointed; with an abundance of soft "moss" covering the outside surface of the bud; with foliaceous parts extending beyond the tip of the bud equal to one-half or less of its length. Color — medium green, occasionally tinted with bronze. As calyx breaks, color — medium red to pink. As first petal opens: same general color (near Rose Bengal 25 or lighter) but showing near base of petal a small greenish yellow area (buds and flowers as grown in plastic greenhoue — Jan. 15, 1976). Color photo shows buds and flowers as they appeared in early October 1975—grown in same house. Color near Dawn Pink 523/3. Size: small.

Bloom: Size when fully open — small, averaging about 1½ inches (4 cm). Petalage — double — 20–30 arranged fairly regularly. Form — slightly cupped at first (showing yellow stamens) and later at maturity becoming more flat with petals rolled loosely outward and downward.

Petals: Fairly thick; satiny both inside and outside. Shape — outside petals, broad lanceolate (almost round with pointed base); intermediate — broad lanceolate with rounded tip; inside—lanceolate with rounded tip.

Color: Newly opened flower from a plant grown in plastic greenhouse (Jan. 15, 1976), Visalia, Calif.

*Outside petal.*—Outside surface — near Rose Madder 23/2 or lighter with small whitish area at base; inside surface — near Rose Madder 23/2 or lighter with small yellowish area at base.

*Intermediate petal.*—Outside surface — same as outside petal or lighter. Inside surface — similar to outside petal.

*Inner petal.*—Outside surface — same as intermediate petal; inside surface — same as intermediate petal. General color effect newly opened flowers — light to very light pink color similar to Fairy Moss (U.S. Plant Pat. No. 3,083) or June Time (U.S. Plant Pat. No. 2,563). Three days open — similar to or lighter than opening color. Behavior — as flowers age petals may become lighter color. Spent petals, may hang on in cool damp weather. Flower longevity (September 1975) — bush in garden or pot 5 to 7 days or longer. Cut flowers at living room temperature 4 to 5 days.

Reproductive Organs:

*Stamens.*—Average number, arranged regularly about pistils.

*Filaments.*—Short, to medium length — yellow.

*Anthers.*—Yellow.

*Pollen.*—Small amount, yellow.

*Pistils.*—Average number.

*Styles.*—Uneven; short; bunched; color— near white.

*Stigma.*—Nearly white or pale yellow-green.

*Ovaries.*—All enclosed in calyx.

*Hips.*—Few (or none), elongated, yellow to orange.

*Sepals.*—Permanent; spear shaped; very mossy.

*Seeds.*—4–6, usually fail to germinate.

Foliage:

*Leaves.*—Compound of five leaflets, abundant; small to moderately small; leathery.

*Leaflets.*—shape: Lanceolate; apex acute; base — rounded acute. Margin serrate. Color: normal green; new growth — usually green. Rachis: medium strength; upper side — several short hairs or prickles; grooved; underside sparsely thorny with numerous very tiny prickles or hairs. Stipules: fairly long; medium width; short length narrow points which may turn out at both more or less than 45°.

Growth:

*Habit.*—Dwarf; bushy; rounded; much branched.

*Growth.*—moderate; vigorous; short to very short internodes.

*Canes.*—Medium; slender — sturdy.

*Main stems.*—Color: medium green. Thorns: numerous; short to medium length; slender; quite straight; color: brown. Prickles — some. Hairs — none.

*Branches.*—Color: medium green. Thorns: numerous, short to medium length, very slender; straight, medium to short oval base. Prickles: some. Hairs: none.

*New shoots.*—Color: normal green. Thorns: numerous; short to medium length; slender, straight, brownish color; sharp points; base oval. Prickles: few. Hairs: may be some.

The miniature rose plant and its flowers as herein described may vary in slight detail due to climatic, soil and cultural conditions under which the variety may be grown; the present description being of the variety as grown in Visalia, Calif.

The following is claimed:

1. A new and distinct variety of miniature moss rose plant of hardy dwarf, rounded, much branched, bush type, as illustrated and described, characterized (1) by buds which are heavily covered with soft moss-like appendages—said "moss" covering the sepals and extending downward onto the peduncle, and (2) by buds and flowers resembling the Baby Pinocchio (U.S. Plant Pat. No. 2,967) miniature rose in general form and size, but less double, the color being a light shade of pink; the general color effect being light pink — of a shade resembling Fairy Moss (miniature—U.S. Plant Pat. No. 3,083); and further characterized by a plant which is of moderate vigor, compact growth habit with short internodes, easy to propagate by budding as well as by cuttings; with small semi-glossy to mat foliage; and flowers, produced recurrently throughout the growing season, borne singly or several to the stem in loose clusters.

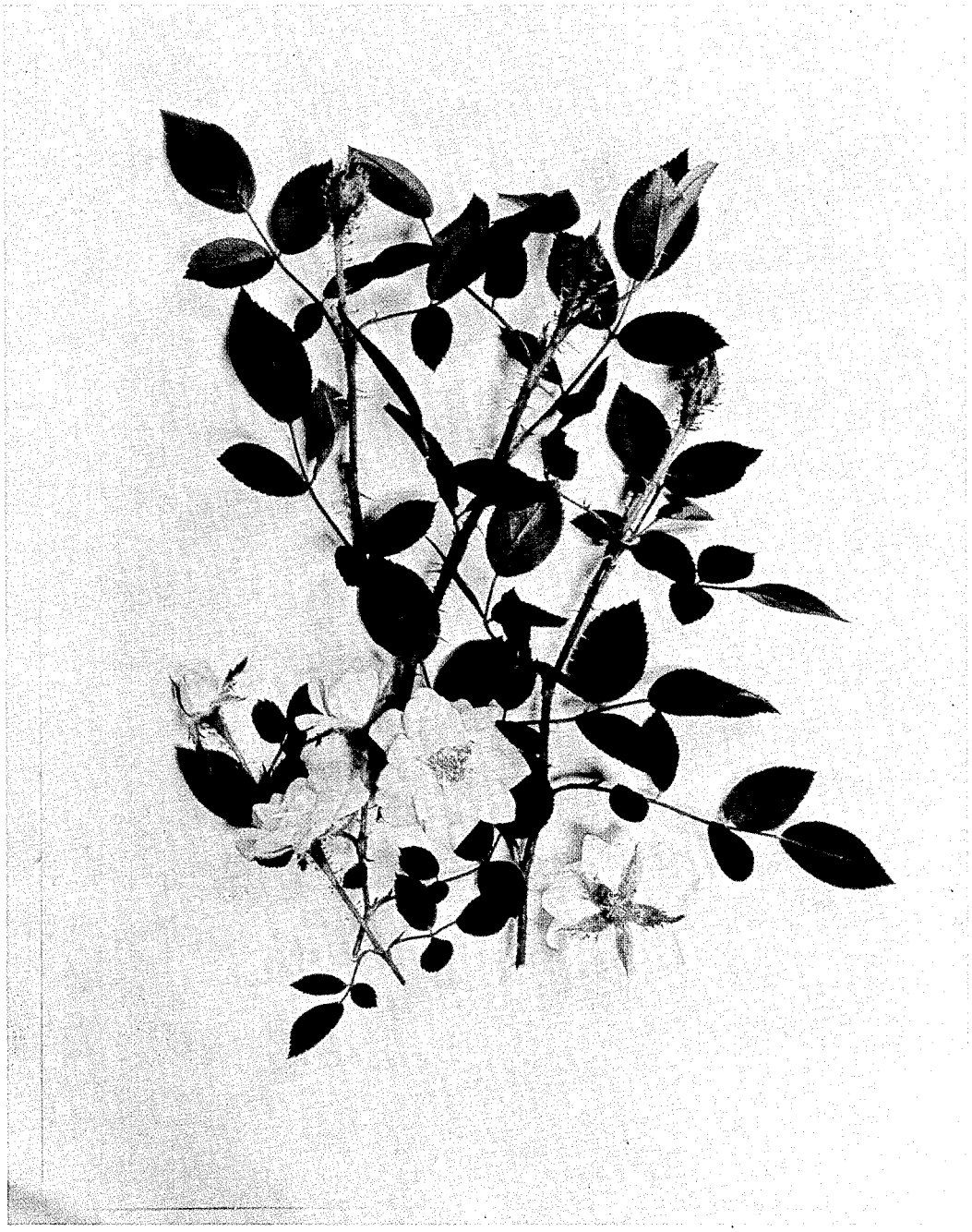

* * * * *